(12) United States Patent
Koo et al.

(10) Patent No.: US 8,058,036 B2
(45) Date of Patent: Nov. 15, 2011

(54) **MICROORGANISM OF *CORYNEBACTERIUM* GENUS HAVING ENHANCED L-LYSINE PRODUCTIVITY AND A METHOD OF PRODUCING L-LYSINE USING THE SAME**

(75) Inventors: Hyun-min Koo, Gyeonggi-do (KR); Sun-young Lee, Daejeon (KR); Young-lyeol Yang, Gyeonggi-do (KR); Hyo-jin Kim, Seoul (KR); Jun-ok Moon, Seoul (KR); Jae-woo Jang, Gyeonggi-do (KR); Sang-jo Lim, Incheon (KR); Jong-soo Choi, Seoul (KR); Young-hoon Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 99 days.

(21) Appl. No.: 12/518,572

(22) PCT Filed: Dec. 28, 2007

(86) PCT No.: PCT/KR2007/006935

§ 371 (c)(1),
(2), (4) Date: Jun. 10, 2009

(87) PCT Pub. No.: WO2008/082180

PCT Pub. Date: Jul. 10, 2008

(65) Prior Publication Data

US 2010/0015673 A1    Jan. 21, 2010

(30) Foreign Application Priority Data

Dec. 29, 2006    (KR) ................. 10-2006-0137651

(51) Int. Cl.
  *C12P 13/08*    (2006.01)
  *C12P 13/04*    (2006.01)
  *C12N 1/20*    (2006.01)
  *C12N 15/74*    (2006.01)
  *C12N 15/00*    (2006.01)

(52) U.S. Cl. ................. 435/115; 435/106; 435/252.32; 435/252.3; 435/471; 435/320.1

(58) Field of Classification Search ................. 435/115, 435/106, 252.32, 252.3, 471, 320.1
See application file for complete search history.

(56) References Cited

U.S. PATENT DOCUMENTS

| | | |
|---|---|---|
| 6,221,636 B1 | 4/2001 | Hayakawa et al. |
| 6,746,855 B2 | 6/2004 | Kreutzer et al. |
| 6,872,553 B2 | 3/2005 | Eikmanns et al. |
| 6,913,909 B2 | 7/2005 | Ziegler et al. |
| 6,962,989 B1 | 11/2005 | Pompejus et al. |
| 7,160,711 B2 | 1/2007 | Bathe et al. |
| 2002/0192674 A1* | 12/2002 | Hermann et al. ............. 435/6 |
| 2002/0197605 A1 | 12/2002 | Nakagawa et al. |
| 2005/0153402 A1 | 7/2005 | Pompejus et al. |
| 2008/0293100 A1 | 11/2008 | Wendisch et al. |
| 2010/0028957 A1 | 2/2010 | Koo et al. |
| 2010/0129884 A1 | 5/2010 | Cho et al. |
| 2010/0330624 A1 | 12/2010 | Jang |

FOREIGN PATENT DOCUMENTS

| | | |
|---|---|---|
| DE | 101 10 760 A1 | 8/2001 |
| JP | H07-121228 | 5/1995 |
| JP | HEI7-121228 | 12/1995 |
| KR | 1020050065712 | 6/2005 |
| KR | 10-2008-025355 A | 3/2008 |
| WO | WO 02/053707 | 7/2002 |
| WO | WO 2005/121349 | 12/2005 |
| WO | WO 2007/039532 | 4/2007 |

OTHER PUBLICATIONS

Database UniProt [Online] Jul. 5, 2004, "SubName: Full=Putative uncharacterized protein".
Ikeda and Nakagawa (Aug. 2003) Appl Microbiol Biotechnol 62:99-109, "The *Corynebacterium glutamicum* genome: features and impacts on biotechnological processes".
Mitsuhashi et al. (Nov. 2006) Biosci. Biotechnol. Biochem. 70(11): 2803-2806, "Disruption of Malate:Quinone Oxidoreductase Increases L-Lysine Production by *Corynebacterium glutamicum*".
Hayes, Finbarr (2003) Annu. Rev. Genet. 37:3-29, "Transposon-Based Strategies for Microbial Functional Genomics and Proteomics".
Mormann (Aug. 10, 2006) BMC Genomics, 7:205, doi:10.1186/1471-2164-205, "Random mutagenesis in *Corynebacterium glutamicum* ATCC 13032 using an IS6100-based transposon vector identified the last unknown gene in the histidine biosynthesis pathway".
Peters-Wendisch et al. (Nov. 2005) Applied and Environmental Microbiology, 71(11):7139-7144, "Metabolic Engineering of *Corynebacterium glutamicum* for L-Serine Production".
Tsuge et al. (2005) Microbiology 151:501-508, "A New Insertion Sequence, ISI4999, from *Corynebacterium glutamicum*".
U.S. Appl. No. 12/867,649, filed Aug. 13, 2010, Jang et al.
Tzvetkov et al. (Jul. 2003) Microbiology 149(7):1659-1673, "Genetic dissection of trehalose biosynthesis in *Corynebacterium glutamicum*: Inactivation of trehalose production leads to impaired growth and altered cell wall lipid composition".
European Search Report issued Dec. 30, 2009 in PCT/KR2007/006935.
Eggeling (1994) Amino Acids 6:261-272, "Biology of L-lysine overproduction by *Corynebacterium glutamicum*".
International Written Opinion dated Jan. 24, 2008 from PCT/KR2007/006936.
International Search Report dated Jan. 24, 2008 from PCT/KR2007/006936.
International Written Opinion dated Jan. 24, 2008 from PCT/KR2007/006935.
International Search Report dated Jan. 24, 2008 from PCT/KR2007/006935.
Office Action issued Jan. 12, 2011 in U.S. Appl. No. 12/518,578.

* cited by examiner

*Primary Examiner* — Ganapathirama Raghu
(74) *Attorney, Agent, or Firm* — Swanson & Bratschun, L.L.C.

(57) ABSTRACT

The present invention relates to a microorganism of *Corynebacterium* genus having enhanced L-lysine productivity and a method of producing L-lysine using the same. More particularly, the present invention relates to a recombinant microorganism of *Corynebacterium* genus having enhanced L-lysine productivity by inactivating endogenous NCgl2534 gene having the amino acid sequence containing repeated lysine residues and a method of producing L-lysine using the same.

6 Claims, 1 Drawing Sheet

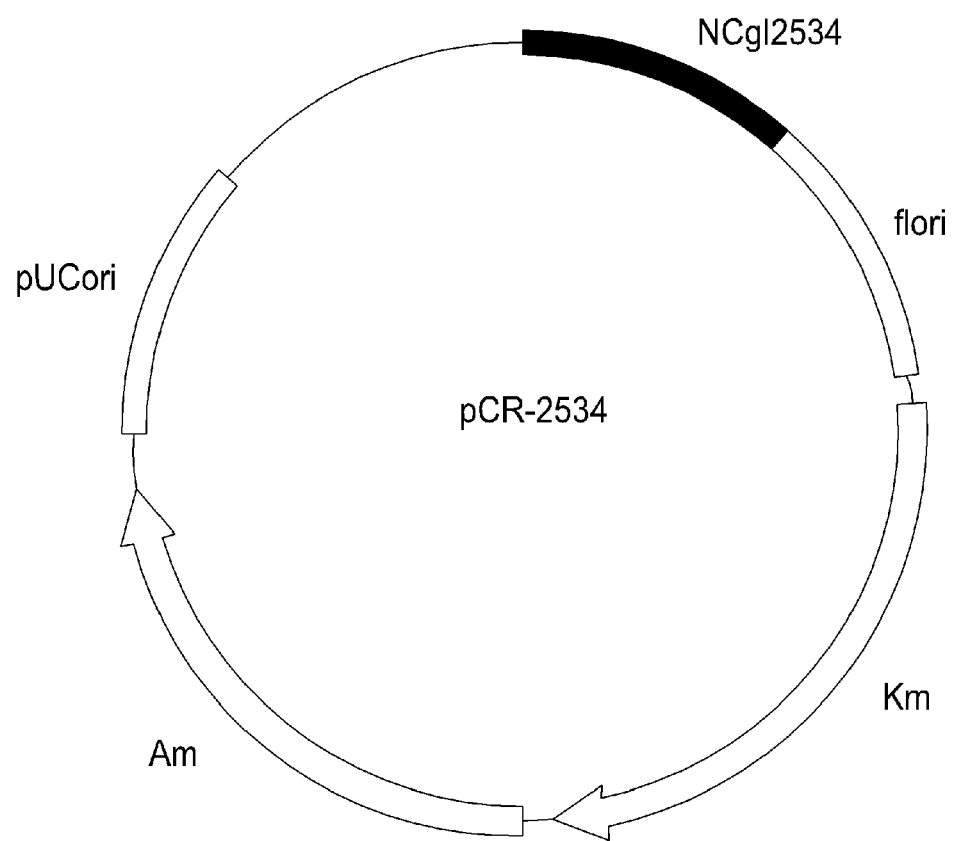
[Fig. 1]

SEQUENCE LISTING

```
<160> NUMBER OF SEQ ID NOS: 7

<210> SEQ ID NO 1
<211> LENGTH: 330
<212> TYPE: DNA
<213> ORGANISM: Corynebacterium glutamicum

<400> SEQUENCE: 1
ttgccggcca aaatcacgga cactcgtccc accccagaat cccttcacgc tgttgaagag      60
gaaaccgcag ccggtgcccg caggattgtt gccacctatt ctaaggactt cttcgacggc     120
gtcactttga tgtgcatgct cggcgttgaa cctcagggcc tgcgttacac caaggtcgct     180
tctgaacacg aggaagctca gccaaagaag gctacaaagc ggactcgtaa ggcaccagct     240
aagaaggctg ctgctaagaa aacgaccaag aagaccacta agaaaactac taaaaagacc     300
accgcaaaga agaccacaaa gaagtcttaa                                      330

<210> SEQ ID NO 2
<211> LENGTH: 297
<212> TYPE: DNA
<213> ORGANISM: Corynebacterium glutamicum

<400> SEQUENCE: 2
cactcgtccc accccagaat cccttcacgc tgttgaagag gaaaccgcag ccggtgcccg      60
caggattgtt gccacctatt ctaaggactt cttcgacggc gtcactttga tgtgcatgct     120
cggcgttgaa cctcagggcc tgcgttacac caaggtcgct tctgaacacg aggaagctca     180
gccaaagaag gctacaaagc ggactcgtaa ggcaccagct aagaaggctg ctgctaagaa     240
aacgaccaag aagaccacta agaaaactac taaaaagacc accgcaaaga agaccac       297

<210> SEQ ID NO 3
<211> LENGTH: 109
<212> TYPE: PRT
<213> ORGANISM: Artificial Sequence
<220> FEATURE:
<223> OTHER INFORMATION: NCgl2534 amino acid sequences encoding a
      hypothetical protein

<400> SEQUENCE: 3

Met Pro Ala Lys Ile Thr Asp Thr Arg Pro Thr Pro Glu Ser Leu His
  1               5                  10                  15

Ala Val Glu Glu Glu Thr Ala Ala Gly Ala Arg Arg Ile Val Ala Thr
             20                  25                  30

Tyr Ser Lys Asp Phe Phe Asp Gly Val Thr Leu Met Cys Met Leu Gly
         35                  40                  45

Val Glu Pro Gln Gly Leu Arg Tyr Thr Lys Val Ala Ser Glu His Glu
     50                  55                  60

Glu Ala Gln Pro Lys Lys Ala Thr Lys Arg Thr Arg Lys Ala Pro Ala
 65                  70                  75                  80
```

-continued

```
Lys Lys Ala Ala Ala Lys Lys Thr Thr Lys Lys Thr Thr Lys Lys Thr
                 85                  90                  95

Thr Lys Lys Thr Thr Ala Lys Lys Thr Thr Lys Lys Ser
            100                 105

<210> SEQ ID NO 4
<211> LENGTH: 20
<212> TYPE: DNA
<213> ORGANISM: Artificial Sequence
<220> FEATURE:
<223> OTHER INFORMATION: primer 1 for amplifying a partial region
      (21-317nt) of NCgl2534

<400> SEQUENCE: 4
cactcgtccc accccagaat                                                 20

<210> SEQ ID NO 5
<211> LENGTH: 20
<212> TYPE: DNA
<213> ORGANISM: Artificial Sequence
<220> FEATURE:
<223> OTHER INFORMATION: primer 2 for amplifying a partial region
      (210317nt) of NCgl2534

<400> SEQUENCE: 5
gtggtcttct ttgcggtggt                                                 20

<210> SEQ ID NO 6
<211> LENGTH: 20
<212> TYPE: DNA
<213> ORGANISM: Artificial Sequence
<220> FEATURE:
<223> OTHER INFORMATION: primer 3 for amplifying NCgl2534 entire gene

<400> SEQUENCE: 6
ttgccggcca aaatcacgga                                                 20

<210> SEQ ID NO 7
<211> LENGTH: 20
<212> TYPE: DNA
<213> ORGANISM: Artificial Sequence
<220> FEATURE:
<223> OTHER INFORMATION: primer 4 for amplifying NCgl2534 entire gene

<400> SEQUENCE: 7
ttaagacttc tttgtggtct                                                 20
```

MICROORGANISM OF *CORYNEBACTERIUM* GENUS HAVING ENHANCED L-LYSINE PRODUCTIVITY AND A METHOD OF PRODUCING L-LYSINE USING THE SAME

RELATED APPLICATIONS

This application is a 35 U.S.C. §371 national phase application of PCT/KR2007/006935 (WO 2008/082180), filed on Dec. 28, 2007, entitled "Microorganism of *Corynebacterium* Genus Having Enhanced L-Lysine Productivity and a Method of Producing L-Lysine Using the Same," which application claims the benefit of Korean Patent Application Serial No. 10-2006-0137651, filed on Dec. 29, 2006. Each of these applications is specifically incorporated herein by reference in its entirety.

TECHNICAL FIELD

The present invention relates to a microorganism of *Corynebacterium* genus having enhanced L-lysine productivity and a method of producing L-lysine using the same. More particularly, the present invention relates to a recombinant microorganism of *Corynebacterium* genus having enhanced L-lysine productivity by inactivating endogenous NCgl2534 gene having the amino acid sequence containing repeated lysine residues and a method of producing L-lysine using the same.

BACKGROUND ART

L-lysine is one of essential amino acids, which has been widely used for animal feed additive, a food additive, a raw material for medicines, etc, and produced by fermentation of the microorganisms of *Corynebacterium* genus.

Microorganisms of *Corynebacterium* genus, particularly *Corynebacterium glutamicum* is a Gram-positive microorganism that are widely used in L-amino acid production. The method of producing L-amino acids using the microorganisms of *Corynebacterium* genus is very important. So, there have been many attempts made to improve the method.

One of the attempts is to improve the microorganisms of *Corynebacterium* genus that produces L-amino acids by disrupting specific genes or attenuation expressing specific genes using a recombinant DNA techniques. For example, U.S. Pat. No. 6,872,553 discloses a method of producing L-lysine of microorganisms of *Corynebacterium* genus by fermentation which comprises the following steps: a) growing microorganisms of *Corynebacterium* genus having an attenuated DNA encoding phosphoenolpyruvate (PEP) carboxykinase (PCK) by one of the mutation method selected from the group consisting of insertion of one or more base pairs in the DNA, deletion of one or more base pairs in the DNA, and transition or transversion of base pairs by introducing a nonsense codon in the DNA or having reduced phosphoenolpyruvate (PEP) carboxykinase (PCK) compared with microorganisms of *Corynebacterium* genus that are not attenuated; b) concentrating desired L-amino acid product in medium or cells; and c) separating L-amino acid.

In addition, many studies on how each gene involved in L-amino acid biosynthesis affects L-amino acid production by amplifying the genes to develop microorganisms of *Corynebacterium* genus have been conducted (Eggeling, Amino Acids 6, 261-272 (1994)). Also, microorganisms of *Corynebacterium* genus can be developed by introducing foreign genes from other bacteria. For example, Japanese Laid-off Patent Publication No. Hei 7-121228 discloses a method of producing L-glutamic acid and L-proline by culturing the microorganism of *Corynebacterium* genus or *Brevibacterium* genus that contain recombinant construct between DNA fragment having genetic information involving synthesis of citric acid synthase and vector DNA, and producing L-glutamic acid and L-proline from the cultures.

However, it is still required to produce a strain with enhanced L-lysine productivity, in spite of the above trials.

DISCLOSURE OF INVENTION

Technical Problem

The present inventors have studied to develop a strain capable of producing L-lysine with high yield with targeting endogenous NCgl2534 gene having repeated lysine residues in its amino acid sequence in a microorganism of *Corynebacterium* genus. And the present inventors tried to increase L-lysine productivity with reducing unnecessary intracellular consumption of lysine by inactivating the target gene above.

It is an object of the present invention to provide a microorganism of *Corynebacterium* genus with enhanced L-lysine productivity.

It is another object of the present invention to provide a method of producing L-lysine using the microorganism above.

Technical Solution

The above objects and other objects of the present invention can be achieved by the following embodiments of the present invention.

The present invention is described in detail hereinafter.

To achieve the above objects, the present invention provides a microorganism having L-lysine productivity, more preferably a microorganism of *Corynebacterium* genus with enhanced L-lysine productivity by inactivating endogenous NCgl2534 gene therein.

In this invention, the microorganism having L-lysine productivity can be selected from the group consisting of *Corynebacterium glutamicum* ATCC 13032, *Corynebacterium thermoaminogenes* FERM BP-1539, *Corynebacterium glutamicum* KFCC 10881, and *Corynebacterium glutamicum* KFCC 11001, but not always limited thereto.

Lysine is functioning as a unit of cell composition or protein synthesis or a regulator. As a unit of cell composition, lysine is used for the synthesis of nucleic acid, amino aid or fat. As a unit of protein synthesis, lysine is used for protein structure or as a major functional group. In particular, as for the unit of protein synthesis, genes translated into proteins are divided into two groups; one is the genes essential for the cell growth, maintenance, and regulation and the other is the genes non-essential for those processes. The non-essential genes are divided as follows; genes not required anymore according to the other genes having equal functions; foreign genes introduced from out side such as virus genes; genes necessary for specific cases but not necessary for any conditions such as for the production of lysine; and genes whose functions have not been explained, yet.

Cells consume lysine massively to compose proteins of the non-essential genes. Therefore, if the non-essential genes are eliminated, it is considered that massive amount of lysine consumption for the non-essential genes can be reduced, which favors the reduction of unnecessary lysine consumption and also favors the production of lysine under the same condition.

To develop a microorganism with improved L-lysine productivity, the present inventors searched a gene that contains lysine residues, the intermediate of lysine biosynthesis, in its amino acid sequence encoding a protein, more than any other genes, from the genome sequence database (NCBI GI: 19553822) of completely analyzed sequence of *Corynebacterium glutamicum* ATCC 13032. As a result, it is confirmed that the repeated lysine residues were presented in C-terminal of NCgl2534 protein having the amino acid sequence represented by SEQ. ID. NO: 3. However, how those repeated lysine residues on the amino acid sequence could be involved in lysine biosynthesis in a strain producing lysine has not been explained.

In this invention, NCgl2534 gene is a gene that endogenously exists in the microorganism of *Corynebacterium* genus, and is known as a gene encoding a hypothetical protein whose functions are unknown. The activity of the gene is predicted from a complete sequence analysis of a genome of *Corynebacterium glutamicum* ATCC 13032 and confirmed to have repeated lysine residues at C-terminal and preferably had the nucleotide sequence represented by SEQ. ID. NO: 1. The endogenous NCgl2534 gene of a microorganism of *Corynebacterium* genus of the present invention preferably has high homology with the sequence represented by SEQ. ID. NO: 1.

In this invention, the "inactivation" can be induced by any inactivation method known to those in the art. The term "inactivation" herein intends to mean that the expression of the NCgl2534 gene is reduced to a low level compared to a wild type strain, or genes that are not expressed and genes that express products having no activity or reduced activity in spite of being expressed are produced.

In this invention, the "inactivation" can be induced by one or more mutation methods selected from the group consisting of insertion of one or more base pairs in NCgl2534 gene, deletion of one or more base pairs in the gene, transition or transversion of base pairs by inserting nonsense codon in the gene.

In a preferred embodiment of the present invention, the microorganism containing the inactivated endogenous NCgl2534 gene can be obtained by culturing a microorganism of *Corynebacterium* genus transformed with the vector containing a part of the NCgl2534 gene and an antibiotic marker in the presence of antibiotics. Preferably, the vector is a pCR-2534 vector containing the NCgl2534 gene fragment of SEQ. ID. NO: 2. The microorganism is transformed with the vector containing a part of the gene sequence, followed by culture in the presence of a selection marker. Then, homologous recombination occurs between a part of the gene and the endogenous gene of the microorganism. By the homologous recombination, the endogenous genes of the microorganism are recombinated and the recombinant gene that contains the marker is only selected by the selection marker. As a result, the microorganism of *Corynebacterium* genus of which endogenous NCgl2534 gene is inactivated can be obtained. However, a method for producing the microorganism of *Corynebacterium* genus according to the present invention is not limited to the homologous recombination, and any method known to those in the art can be used.

The transformed microorganism with improved L-lysine productivity of the present invention may be *Corynebacterium glutamicum* KFCC10881-CO01-0019 (Accession No: KCCM 10811P).

The present invention also provides a method of producing L-lysine using the transformed microorganism. More particularly, the present invention provides a method of producing L-lysine comprising the steps of producing L-lysine in cultures or cells by culture of the microorganism of *Corynebacterium* genus; and collecting L-lysine from the cultures.

In the method of the present invention, the culture of microorganism of the *Corynebacterium* genus can be performed by any culture method and culture conditions known to those in the art.

The medium for the culture of the microorganism of *Corynebacterium* genus can be selected from those described in Manual of Methods for General Bacteriology by the American Society for Bacteriology (Washington D.C., USA, 1981).

The medium includes various carbon sources, nitrogen sources and trace elements. The carbon source is exemplified by sugar and carbohydrate such as glucose, sucrose, lactose, fructose, maltose, starch, cellulose; oil and fat such as soybean oil, sunflower oil, castor oil and coconut oil; fatty acid such as palmitic acid, stearic acid, and linoleic acid; alcohol such as glycerol and ethanol; and organic acid such as acetic aid. One of these compounds or a mixture thereof can be used as a carbon source.

The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source.

The medium herein can additionally include potassium dihydrogen phosphate, dipotassium hydrogen phosphate and corresponding sodium-containing salts as a phosphate source. The medium can also include a metal salt such as magnesium sulfate or iron sulfate. In addition, amino acids, vitamins and proper precursors can be added as well. The medium or the precursor can be added to the culture by batch-type or continuously.

The PH of the culture can be controlled using a basic compound such as sodium hydroxide, potassium hydroxide or ammonia, or an acid compound such as phosphoric acid or sulfuric acid during the cultivation. The generation of air bubbles can be inhibited during the cultivation by using an antifoaming agent such as fatty acid polyglycol ester. To maintain aerobic condition of the culture, oxygen or oxygen-containing gas (ex, air) can be injected into the culture. The temperature of the culture is preferably 20-45° C., more preferably 25-40° C. The cultivation can be continued until the production of L-amino acid reaches a wanted level, and the preferable culture time is 10-160 hours.

In this method, the culture can be performed in a continuous or batch type method such as batch, fed-batch and repeated fed-batch cultures. It is well understood by those in the art that the culture method can be selected appropriately.

L-amino acid may be separated and analyzed by anion exchange chromatography and following ninhydrin derivatization.

In addition to the identification of the gene, the present inventors further inactivated NCgl2534 gene, the endogenous gene of the microorganism of *Corynebacterium* genus, to measure the lysine productivity. And as a result, it was confirmed that the lysine productivity was increased.

BRIEF DESCRIPTION OF THE DRAWINGS

The application of the preferred embodiments of the present invention is best understood with reference to the accompanying drawings, wherein:

FIG. 1 is a diagram showing the pCR-2534 vector wherein 296 bp NCgl2534 gene fragment was cloned.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

In the following examples, to confirm the effect of NCgl2534 gene having repeated lysine residues in its amino acid sequence on the production of lysine, NCgl2534, the endogenous gene of *Corynebacterium glutamicum* KFCC10881 was inactivated. And the microorganism containing the inactivated NCgl2534 gene was cultured and the lysine productivity was measured.

EXAMPLE 1

Construction of a Vector for Inactivating NCgl2534 Gene, the Endogenous Gene of the Microorganism of *Corynebacterium* Genus In this example, 296 bp fragment of the NCgl2534 gene (SEQ. ID. NO: 2) ($21^{st}$-$317^{th}$ nucleotides of the sequence represented by SEQ. ID. NO: 1) was amplified by PCR using chromosomal DNA of *Corynebacterium glutamicum* (ATCC 13032) as a template with oligonucleotide primers represented by SEQ. ID. NO: 4 and NO: 5 to construct NCgl2534 gene disruption vector containing a part of the endogenous NCgl2534 gene and an antibiotic marker. PCR was performed as follows; denaturation at 96° C. for 30 seconds, annealing at 52° C. for 30 seconds and polymerization at 72° C. for 30 seconds (30 cycles). The amplified NCgl2534 gene fragment was cloned into *E. coli* plasmid pCR.2.1 by using TOPO cloning kit (Invitrogen, USA). As a result, pCR-2534 vector was constructed. FIG. 1 is a diagram showing the pCR-2534 vector that 296 bp NCgl2534 gene fragment was cloned.

EXAMPLE 2

Construction of a Microorganism Producing L-lysine Having Inactivated NCgl2534 Gene, the Endogenous Gene of *Corynebacterium glutamicum* KFCC10881

*Corynebacterium glutamicum* KFCC10881, a microorganism producing L-lysine, was transformed with the pCR-2534 vector constructed in example 1 by electric pulse method according to the method described in Appl. Microbiol. Biotechnol. (1999) 52:541-545. PCR was performed on the $2^{nd}$ day of culture to confirm the disruption of the NCgl2534 gene in the transformed microorganism. Particularly, PCR was performed using chromosomal DNA of the transformed microorganism as a template with oligonucleotide primers represented by SEQ. ID. NO: 6 and NO: 7. As a result, approximately 5020 bp ($1^{st}$-$330^{th}$ nucleotides of the sequence represented by SEQ. ID. NO: 1) NCgl2534 gene fragment containing pCR-2534 plasmid was amplified. From the PCR, it was confirmed that the NCgl2534 gene was disrupted by insertion of pCR-2534 plasmid into the middle of the endogenous NCgl2534 gene on chromosomal DNA by cross-over through homologous recombination.

The obtained microorganism was named "*Corynebacterium glutamicum* KFCC10881-CO01-0019", which was deposited at KCCM (Korean Culture Center of Microorganisms) of KFCC (Korean Federation of Culture Collection), the International Depository Authority located at 361-221, Hongje-1-Dong, Seodaemungu-Gu, Seoul, Korea, on Dec. 7, 2006 (Accession No: KCCM 10811P).

EXAMPLE 3

Production of Lysine by Using *Corynebacterium glutamicum* KFCC10881-CO01-0019

The transformant *Corynebacterium glutamicum* KFCC10881-CO01-0019 (KCCM 10811P) prepared in example 2 was cultured to produce L-lysine.

First, the *Corynebacterium glutamicum* mother strain KFCC10881 and the transformant KFCC10881-CO01-0019 (KCCM 10811P) were inoculated in a 250 ml corner-baffled flask containing 25 ml of the seed culture having the following composition, followed by culture at 30° C. for 20 hours with stirring at 200 rpm. 1 mL of the seed culture was inoculated in a 250 ml corner-baffled flask containing 24 ml of the production medium having the following composition, followed by culture at 30° C. for 120 hours with stirring at 200 rpm. Upon completion of the culture, L-lysine production was measured by HPLC (Waters 2457).

As a result, the *Corynebacterium glutamicum* mother strain KFCC10881 and the *Corynebacterium glutamicum* KFCC10881-CO01-0019 (KCCM 10811P) produced 45 g/l and 52 g/l of L-lysine in their culture media respectively as hydrochloride of L-lysine.

Seed Medium (pH 7.0):
Raw sugar 20 g, Peptone 10 g, Yeast extract 5 g, Urea 1.5 g, $KH_2PO_4$ 4 g, $K_2HPO_4$ 8 g, $MgSO_4 7H_2O$ 0.5 g, Biotin 100 ▯, Thiamine HCl 1000 ▯, Calcium-pantothenic acid 2000 ▯, nicotinamide 2000 ▯ (in 1 liter of process water)

Production Medium (pH 7.0):
Raw sugar 100 g, $(NH_4)_2SO_4$ 40 g, Soybean protein 2.5 g, Corn Steep Solids 5 g, Urea 3 g, $KH_2PO_4$ 1 g, $MgSO_4 7H_2O$ 0.5 g, Biotin 100 ▯, Thiamine HCl 1000 ▯, Calcium-pantothenic acid 2000 ▯, Nicotinamide 3000 ▯, $CaC_3O$ 30 g (in 1 liter of process water)

EXAMPLE 4

Collection of L-lysine From the *Corynebacterium glutamicum* KFCC 10881-CO01-0019 Culture

*Corynebacterium glutamicum* KFCC10881-CO01-0019 was cultured in the medium containing molasses and raw sugar. pH of 1 L of the obtained lysine culture was adjusted to 2.0 using HCl and then Ca ions were changed into the form of $CaSO_4$ or $CaCl_2$. The culture was spilled on the cation exchange resin revived as ammonium ions (Diaion SK-L10) upwardly, followed by adsorption. The cells remaining in the resin layer were eliminated by washing with desalted water, followed by elution using 2 N ammonium hydroxide. As a result, lysine was collected at high concentration. The collected solution containing lysine was concentrated and pH of the solution was regulated as 5.0 by HCl, followed by cooling crystallization at 20° C. After crystallization, the obtained slurry was centrifuged to give the primary wet product. The mother solution was concentrated by batch-type, followed by crystallization to obtain the secondary wet product. The primary and the secondary wet products were mixed and dried to give 47.5 g of dried lysine product (lysine content: 98.5%).

INDUSTRIAL APPLICABILITY

As explained hereinbefore, according to the present invention, L-lysine productivity can be increased by inactivating NCgl2534 gene, the endogenous gene of *Corynebacterium*

*glutamicum* KFCC10881-CO01-0019 (KCCM 10811P). The method of the present invention facilitates the production of L-lysine at high concentration, resulting in the increase of L-lysine productivity.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated *Corynebacterium glutamicum* microorganism having enhanced L-lysine productivity by inactivating the endogenous NCgl2534 gene having the nucleotide sequence of SEQ. ID. NO:1 with repeated lysine residues in its amino acid sequence, wherein said inactivation is induced by one or more mutation methods selected from the group consisting of insertion of one or more base pairs in the gene, deletion of one or more base pairs in the gene, transition or transversion of base pairs by inserting nonsense codon in the gene.

2. The *Corynebacterium glutamicum* according to claim 1, wherein said inactivation is induced by transformation of the *Corynebacterium glutamicum* with a vector comprising part of the endogenous NCgl2534 gene and an antibiotic marker.

3. The *Corynebacterium glutamicum* according to claim 2 is *Corynebacterium glutamicum* KFCC 10881-0001-0019 (KCCM 10811P) selected by culture in the presence of antibiotics.

4. A method of producing L-lysine comprising the steps of:
   producing L-lysine in cultures or cells by culture of an isolated *Corynebacterium glutamicum* microorganism having enhanced L-lysine productivity by inactivating the endogenous NCgl2534 gene having the nucleotide sequence of SEQ. ID. NO:1 with repeated lysine residues in its amino acid sequence, wherein; said inactivation is induced by one or more mutation methods selected from the group consisting of insertion of one or more base pairs in the gene, deletion of one or more base pairs in the gene, transition or transversion of base pairs by inserting nonsense codon in the gene, and
   collecting L-lysine from the cultures.

5. The method according to claim 4, wherein said inactivation is induced by transformation of the *Corynebacterium*

*glutamicum* with a vector comprising part of the endogenous NCg12534 gene and an antibiotic marker.

6. The method according to claim 5, wherein the *Corynebacterium glutamicum* is *Corynebacterium glutamicum* KFCC 10881-0001-0019 (KCCM 10811P) selected by culture in the presence of antibiotics.

* * * * *